US 6,626,946 B1

(12) United States Patent
Walch et al.

(10) Patent No.: US 6,626,946 B1
(45) Date of Patent: Sep. 30, 2003

(54) SHOULDER PROSTHESIS AND HUMERAL STEMS FOR SUCH A PROSTHESIS

(75) Inventors: Gilles Walch, Lyons (FR); Pascal Boileau, Nice (FR)

(73) Assignee: Tornier SA, Saint-Ismier (FR)

( * ) Notice: Subject to any disclaimer, the term of this patent is extended or adjusted under 35 U.S.C. 154(b) by 0 days.

(21) Appl. No.: 09/363,407

(22) Filed: Jul. 29, 1999

Related U.S. Application Data

(63) Continuation of application No. 08/882,085, filed on Jun. 25, 1997, now abandoned.

(30) Foreign Application Priority Data

Jun. 25, 1996 (FR) .............................................. 96 08152

(51) Int. Cl.$^7$ ................................................. A61F 2/40
(52) U.S. Cl. ................................................. 623/19.11
(58) Field of Search ........................... 623/19.11, 19.12, 623/19.13, 19.14

(56) References Cited

U.S. PATENT DOCUMENTS

| 4,919,670 | A | * | 4/1990 | Dale et al. ................ 623/19.14 |
| 5,358,526 | A | * | 10/1994 | Tornier ..................... 623/19.14 |
| 5,702,486 | A | * | 12/1997 | Craig et al. ............... 623/19.14 |
| 5,910,171 | A | * | 6/1999 | Kummer et al. ......... 623/19.14 |
| 5,944,758 | A | * | 8/1999 | Mansat et al. ........... 623/19.14 |

* cited by examiner

*Primary Examiner*—Bruce Snow
(74) *Attorney, Agent, or Firm*—Dowell & Dowell, P.C.

(57) ABSTRACT

A prosthesis of the upper extremity of the humerus of the type that comprises a stem anchored in the humeral canal and provided on its upper or metaphyseal part with a bearing surface against which rests a hemispherical cap suitable to interact with a shoulder socket, wherein the stem is selected from a set of stems each provided with a bearing surface having a tilt angle that differs with respect to a longitudinal axis of each stem. A set of humeral stems comprises several stems each of which is provided with a bearing surface having a tilt angle that differs with respect to the longitudinal axis of each stem.

4 Claims, 1 Drawing Sheet

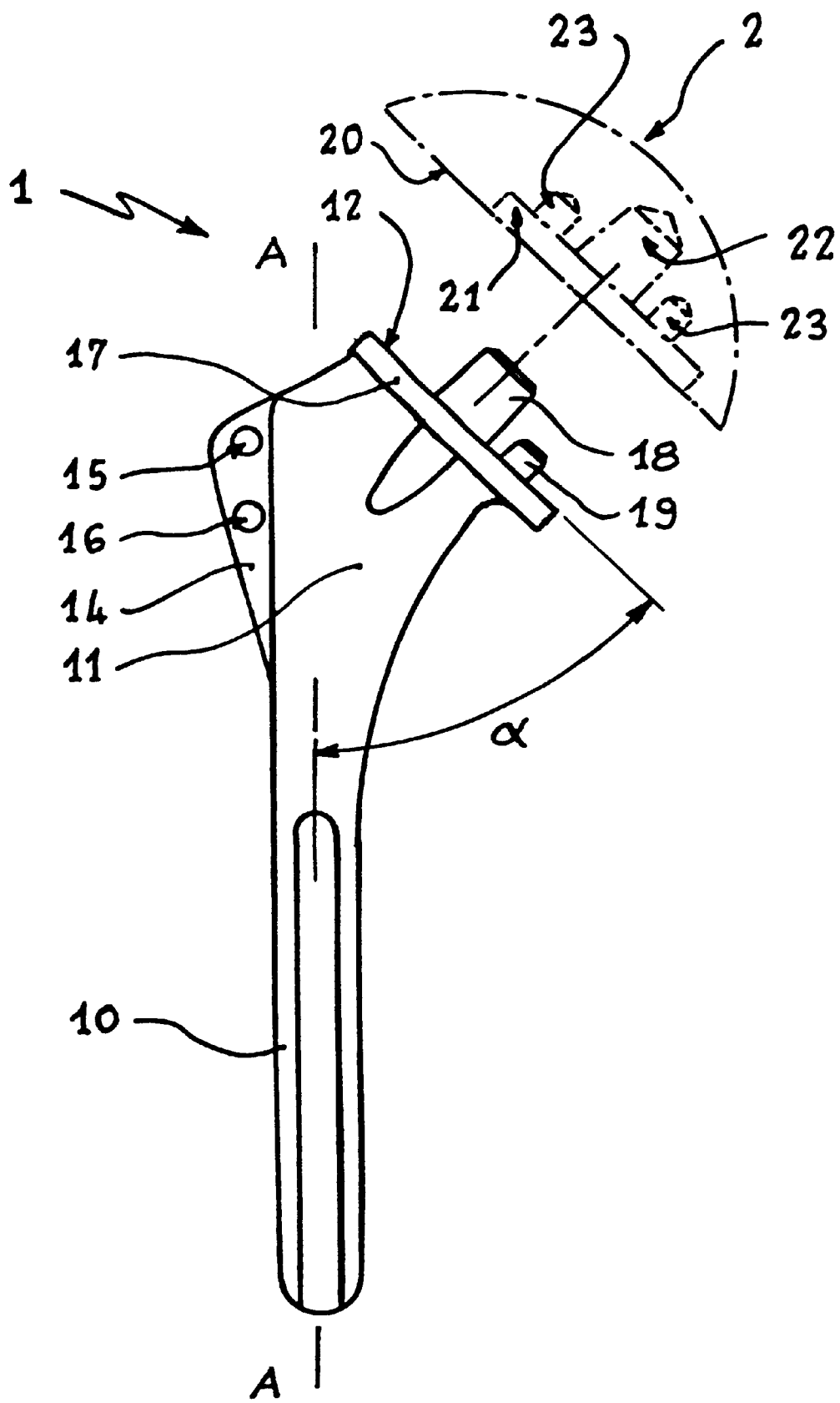

SHOULDER PROSTHESIS AND HUMERAL STEMS FOR SUCH A PROSTHESIS

CROSS REFERENCE TO RELATED APPLICATIONS

This application is a continuation of U.S. patent application, Ser. No. 08/882,085 filed Jun. 25, 1997, now abandoned entitled SHOULDER PROSTHESIS AND HUMERAL STEMS FOR SUCH A PROSTHESIS by the same inventors.

BACKGROUND OF THE INVENTION

1. Field of the Invention

The present invention relates to a prothesis of the upper extremity of the humerus, which prosthesis is of the type that comprises a stem anchored in the humeral canal and which is provided on its upper part with a bearing surface against which rests a hemispherical cap suitable to interact with the shoulder socket. The invention relates also to a set of humeral stems for such a prosthesis.

2. History of the Related Art

Well known are prostheses of this type that comprise a humeral stem that on its upper part presents a bearing surface provided with a clamping device for the fastening of a hemispherical cap. The humeral stem has only one bearing surface suitable to accommodate the cap. Under these conditions, the cap is at a fixed tilt angle and it does not cover in a satisfactory manner the cut plane of the extremity of the humerus so that it becomes necessary to adapt the bone to the prosthesis with all the anatomic consequences it entails.

Furthermore, in patent application EP-A1-0 549 480, a prothesis is disclosed for the upper extremity of the humerus that enables:

- an effective positioning and anchoring in the humeral canal;
- the recovery of the entire height of the reconstituted humerus;
- a diameter of the humeral cap suitable to ensure a satisfactory covering of the cut plane of the humerus;
- a satisfactory tilt angle of the humeral cap;
- an appropriate retro-torsion angle of the humeral cap;
- a lateral offset of the cap with respect to the humeral axis;
- an anteroposterior positioning of the cap with respect to the humeral axis; and
- an appropriate height of the humeral cap.

Thus, the prosthesis disclosed in patent application EP-A1-0 549 480 comprises a stem that is anchored in the humeral canal, one hemispheric cap suitable to interact with the shoulder socket, and a wedge-shaped cross piece suitable to adjust the distance from the base of the cap with respect to the bearing surface of the stem. The cross piece also allows the direction of the base of the cap to be changed with respect to the plane including the stem's bearing surface by changing the angle determined by its end surfaces. Moreover, this prosthesis comprises means to adjust the angular position of the cap around an eccentric geometric axis with respect to its own geometric axis.

This type of prosthesis has certain drawbacks as regards the disposition of several independent elements that the surgeon must fit together when operating, in order to obtain a perfect repair of the shoulder articulation. This specific disposition is quite complex. It requires long and difficult manipulations by part of the surgeon to obtain the exact positioning of the hemispheric cap with respect to the osseous cut.

SUMMARY OF THE INVENTION

The prosthesis of the upper extremity in accordance with the invention has as an objective to provide the surgeon with the possibility of cutting the neck of the humerus according to an anatomic line clearly separating the articular portion from the osseous metaphysis.

With this in mind, the invention relates to a prosthesis of the upper extremity of the humerus of the type that comprises a stem anchored in the humeral canal, which stem is provided on its upper or metaphyseal part with a bearing surface against which rests a hemispherical cap suitable to interact with the shoulder socket, characterized by the fact that the stem is chosen from among a set of stems, each of which has a bearing surface of different tilt angle with respect to the longitudinal axis of each stem.

With the invention, the surgeon is not limited to the direction he cuts, separating the articular portion from the osseous metaphysis. Thus, he can follow exactly the anatomy of the shoulder being operated on. According to the size of the patient, the surgeon then selects a set of several stems, e.g., 4 or 6. Then, the surgeon selects from this set of stems the stem for the prosthesis that, with respect to the tilt angle of its bearing surface, adapts best to the cut he made beforehand, in order to position with utmost precision the hemispherical cap on the frontal plane. The prosthesis in accordance with the present invention has the additional advantage that each stem may be manufactured in a single piece, in contrast to the adjustable prostheses that require several parts to be fitted together during an operation.

A first advantage of the present invention is that the bearing surface of each stem is provided with a round collar for the housing of a hemispheric cap.

The design can also be such that the round collar of each stem fits with reduced play into an eccentric housing on the base of the hemispheric cap. Such a structure allows a direct and easy fitting of the humeral stem on the spherical cap.

The present invention relates also to a set of humeral stems for a prosthesis of the upper extremity of the humerus, comprising several stems, each of which is provided with a bearing surface presenting a different tilt angle with respect to the longitudinal axis of each stem. Such a set of stems can be designed in several sizes that correspond to the possible different sizes of the patient; the diameter of the diaphysis can be between 6 and 15 mm.

According to an advantageous aspect of the set of stems of the present invention, a hemispheric cap is provided to interact with the bearing surface of each stem. This corresponds to the modular nature of the invention.

According to another advantageous aspect of the present invention, the hemispheric cap comprises a base provided with an eccentric housing into which fits, with reduced play, a circular collar that constitutes the bearing surface of each stem.

In this case, the circular collar of each stem, constituting the set of stems, can be designed in such a manner that it is tilted at a different angle with respect to the longitudinal axis of each stem.

BRIEF DESCRIPTION OF THE DRAWINGS

By way of example, the accompanying drawing will allow a better understanding of the invention, of its characteristics and of the benefits it is likely to provide. The single drawing is a front view illustrating a prosthesis for the upper extremity of the humerus in which the bearing surface is tilted at an angle that differs for each stem in a set in order to adapt to the osseous cut performed by a surgeon.

DESCRIPTION OF THE PREFERRED EMBODIMENT

The drawing shows a prosthesis 1 of the upper extremity of the humerus comprising a stem 10 that is anchored in the humeral canal and that is provided at its upper part 11 with a bearing surface 12 against which rests a hemispheric cap 2 suitable to interact with the shoulder socket.

The stem 10 has a cylindrical section that fits into the humeral canal and whose upper or metaphyseal part 11 is shaped following a rectilinear outer contour. The metaphyseal part 11 includes on the sagittal plane a slightly lateral conical shape of its sides. The metaphyseal or upper part 11 is formed as one piece with a flange 14 on the outer surface of the stem 10, which flange has two openings 15, 16 that allow, in case of fractures, a reconstitution of the upper extremity of the humerus around the prosthesis.

Opposite the flange 14, the stem 10 ends in a bearing surface 12, constituted by a circular collar 17 that is tilted at an angle α with respect to the longitudinal axis A—A of the stem 10. This angle α is fixed for each stem 10 and different for the stems of the same set, constituting thus a set of stems whose bearing surfaces 12 and their respective circular collars 17 are arranged on differently tilted planes.

Thus the angle α can be equal to 50° or 45° or 40° or 35° for each stem constituting the set of humeral stems. In such a case, the set of stems comprises four stems. Each set may be constituted by several stems 10 having an angle α different than those mentioned above, that is to say, it is constituted by more than four stems, in order to increase the surgeon's selection after he has performed the cutting of the neck of the humerus according to the necessary tilt in order to place the hemispheric cap 2 in a precise position on the frontal plane. In fact, the surgeon cuts the neck of the humerus according to an anatomic line that clearly separates the articular part from the osseous metaphysis. Once the cut is performed, the surgeon selects the stem 10 from the set of stems, so that the stem perfectly adapts to the previously performed cut, in order to place in a precise manner the cap 2 on the frontal plane.

In practice, for each size of patient, the set of stems comprises between 4 and 10 stems.

The circular collar 17 is firmly joined in its middle to a truncated cone-shaped piece 18 that extends perpendicular to the bearing surface 12. Near the truncated cone-shaped piece 18 is a stud 19 that extends perpendicular to the bearing surface 12.

The hemispheric cap 2 includes a base 20 on which is arranged in an eccentric manner a circular recess 21 the diameter of which nearly corresponds to that of the collar 17 of the bearing surface 12 of the stem 10. In the center of the circular recess is a truncated cone-shaped bore 22 the diameter of which corresponds to that of the piece 18 of the metaphyseal part 11 of the stem 10. The bottom of the recess 21 has a number of holes 23 that are concentric to its center. The assembly of the hemispheric cap 12 with respect to the metaphyseal part 11 of the stem 10 is effected by fitting the truncated cone-shaped piece 18 into the bore 22, the circular collar 17 being adjusted in the recess 21 while the stud 19 of the collar 17 is inserted into one of the holes 23 of the hemispheric cap 2. It is understood that because of the conicity of about 6° of the stud 18 and of the bore 22, the two elements are fitted together by wedging.

As stated above, one has a set of stems 10 each having a bearing surface 12 tilted at a different angle α, so that the tilting of the hemispheric cap 2 can be set according to the osseous cut performed beforehand by the surgeon.

Also, one may have available a consequent number of hemispheric caps 2 of different diameters, each of which corresponds to a given height depending on the case of surgery.

Because of the structure of the base of the hemispheric cap 2, one can modify the anteroposterior positioning of the cap with respect to the humeral axis in order to adapt it to all the positions necessary to perform the normal function of the treated shoulder. Furthermore, because of the different positions of the hemispheric cap 2, its anatomic positioning can be changed in such a manner that it can be applied either to the left or the right side.

We claim:

1. A humeral prosthesis set for the upper extremity of the humerus, the set comprising; a plurality of single piece stems each of which includes a portion which is adapted to be anchored in a humeral canal and each of which includes an upper metaphyseal part having a bearing surface which is oriented at a tilt angle with respect to a longitudinal axis of each stem, said bearing surface of each stem of the set being oriented at a tilt angle with respect to the longitudinal axis of the stem such that each tilt angle differs from a tilt angle of the bearing surfaces of other stems of the set, the set including at least one hemispherical cap adapted to be seated against the bearing surface of one of the stems selected from said plurality of stems, and said at least one hemispherical cap being adapted to interact with a shoulder socket.

2. The prosthesis set of claim 1, wherein said bearing surface of each stem of said plurality of stems is defined by a circular collar adapted to be seated within a recess formed in a base of said at least one hemispheric cap.

3. The prosthesis set of claim 2, including a truncated cone-shaped piece extending perpendicular outwardly from a central portion of each of said collars, and a stud extending outwardly in spaced relationship to said truncated cone-shaped piece from each of said collars.

4. The prosthesis set of claim 3, wherein said recess is generally circular and is eccentric with respect to said base of said hemispherical cap, said base having a bottom, a truncated cone-shaped blind hole and a series of concentric holes surrounding said blind hole in said bottom of said recess which are adapted to receive said truncated cone-shaped piece and said stud, respectively, of one of said plurality of stems in order to secure said hemispherical cap to said collar of said one of said stems.

\* \* \* \* \*